United States Patent [19]

Green et al.

[11] Patent Number: 4,573,622
[45] Date of Patent: Mar. 4, 1986

[54] SURGICAL FASTENER APPLYING APPARATUS WITH VARIABLE FASTENER ARRAYS

[75] Inventors: David T. Green, Norwalk; Edgar D. Gunning, Danbury, both of Conn.

[73] Assignee: United States Surgical Corporation, Norwalk, Conn.

[21] Appl. No.: 662,678

[22] Filed: Oct. 19, 1984

[51] Int. Cl.[4] .......................... A61B 17/04; B25C 5/00
[52] U.S. Cl. ................................. 227/19; 128/334 R; 227/DIG. 1
[58] Field of Search ...................... 128/334 R, 334 C; 227/19, DIG. 1

[56] References Cited

U.S. PATENT DOCUMENTS

4,402,444  9/1983  Green .................................. 227/19
4,470,533  9/1984  Schuler ............................... 227/19

Primary Examiner—Anton O. Oechsle
Attorney, Agent, or Firm—Robert R. Jackson; John E. Nathan

[57] ABSTRACT

Apparatus for applying an array of surgical fasteners. The apparatus includes a work transmitting member removably interposable between the member which supplies the fastener applying work and a subset of the fasteners in the array so that the subset can be applied or not applied at the option of the user.

5 Claims, 15 Drawing Figures

SURGICAL FASTENER APPLYING APPARATUS WITH VARIABLE FASTENER ARRAYS

BACKGROUND OF THE INVENTION

This invention relates to surgical fastener applying apparatus, and more particularly to apparatus for substantially simultaneously applying a plurality of surgical fasteners to body tissue in a predetermined array.

Illustrative of the known devices for applying arrays of surgical fasteners are those of the type shown in Hirsch et al. U.S. Pat. No. 3,275,211 and Green U.S. Pat. No. 4,402,445. The Hirsch et al. device applies a longitudinal array of metal surgical staples to body tissue clamped between a staple holder and an anvil. The Green device applies a longitudinal array of initially two-part non-metallic fasteners to body tissue similarly clamped between a fastener holder and an anvil. The term "surgical fastener" as used herein is generic to both of the foregoing types of staples or fasteners.

In some surgical procedures it is desirable to omit some of the fasteners from the array. For example, in one well known surgical procedure, an array of surgical fasteners is applied across a major portion of the stomach to reduce the capacity of the stomach. Only a relatively small lumen is left at one end of the fastener array. This procedure is facilitated by clamping across the entire stomach. However, most of the available fastener applying instruments apply fasteners substantially coextensively with the area of tissue clamped by the instrument. In order to leave the desired lumen, it is necessary to remove some of the staples from the instrument before using it. This is an undesirable added step in the use of the instrument.

It is therefore an object of this invention to provide surgical fastener applying instruments in which the array of fasteners applied by the instrument can be more easily varied by the user of the instrument.

It is another object of the invention to provide surgical fastener applying instruments in which the array of fasteners applied by the instrument can be varied without removing unneeded fasteners from the instrument.

SUMMARY OF THE INVENTION

These and other objects of the invention are accomplished in accordance with the principles of the invention by providing surgical fastener applying apparatus in which the means for transmitting to the fasteners the work required to apply them includes means for optionally not transmitting work to a subset of the fasteners. In a preferred embodiment this is accomplished by having a work transmitting member removably interposed between the member which supplies the fastener applying work and a subset of the fasteners. When the fastener subset is to be applied, the work transmitting member is interposed between the work supplying member and the subset. When the fastener subset is not to be applied, the work transmitting member is not interposed between the work supplying member and the subset.

Further features of the invention, its nature and various advantages will be more apparent from the accompanying drawings and the following detailed description of the invention.

DETAILED DESCRIPTION OF THE INVENTION

Figure 1:
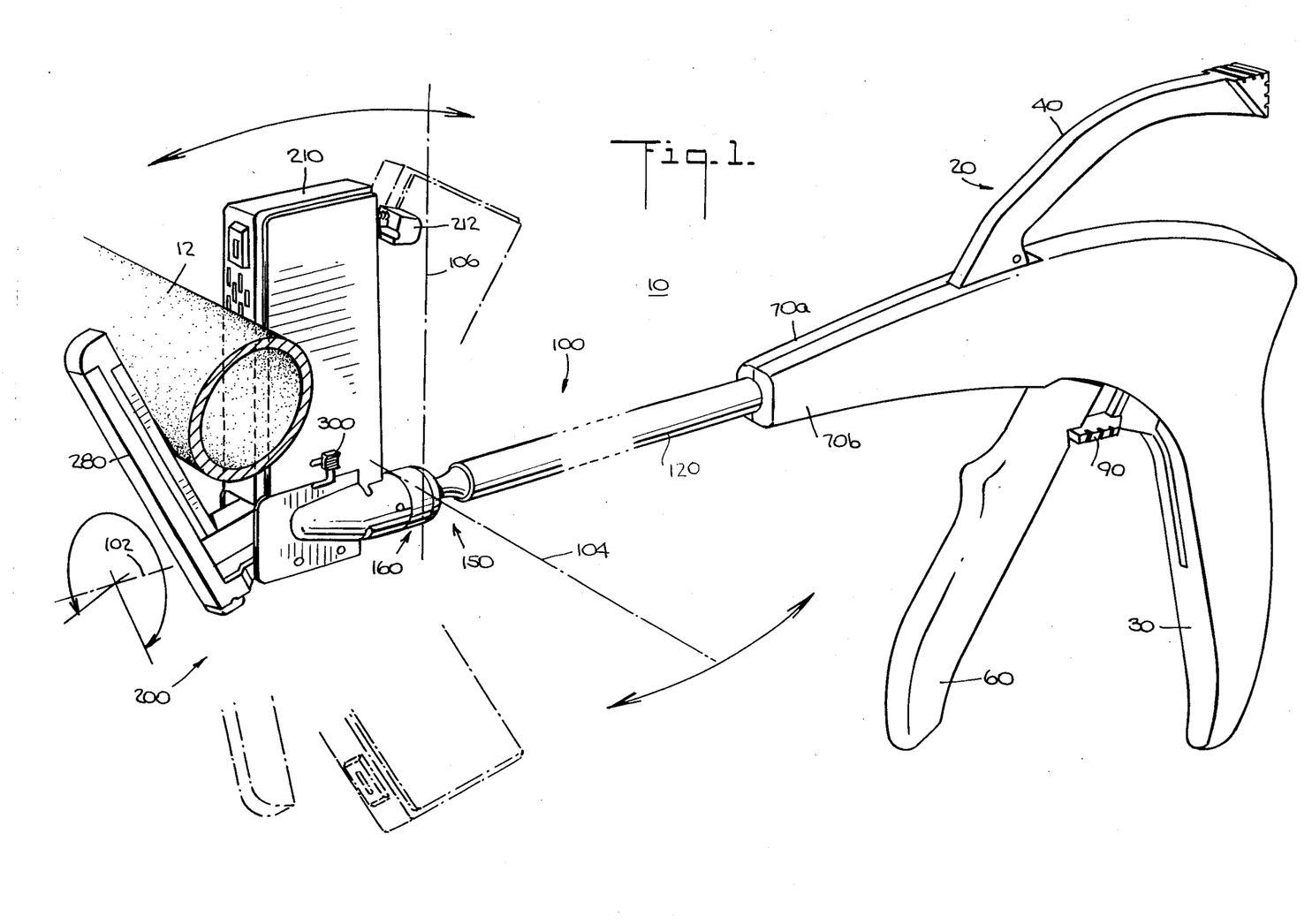
FIG. 1 is a perspective view of an illustrative embodiment of the invention.

As shown in FIG. 1, an illustrative embodiment of the surgical fastener applying apparatus or instrument 10 of this invention includes proximal actuator assembly 20, distal fastener applying assembly 200, and intermediate shaft assembly 100.

Fastener applying assembly 200 includes proximal fastener holding part 210 and distal anvil part 280. Anvil part 280 is mounted for limited pivotal and translational motion relative to fastener holding part 210 so that anvil part 280 can be translated and pivoted away from fastener holding part 210 as shown in solid lines in FIG. 1 to permit the tissue 12 that is to be fastened to be inserted between the distal surface of fastener holding part 210 and the proximal surface of anvil part 280.

Fastener holding part 210 is connected to the distal end of shaft assembly 100 just beyond an articulation or joint 150 in the shaft assembly. In the illustrative embodiment, joint 150 comprises a spherical ball 152 (FIG. 2) rotatably secured in a complementary socket 160. Joint 150 allows fastener applying assembly 200 to rotate about each of three mutually orthogonal axes 102, 104, and 106, all of which intersect at the center of ball 152. A few of the possible positions of fastener applying assembly 200 are suggested in phantom lines in FIG. 1. The proximal end of shaft assembly 100 may also be rotatably mounted in actuator assembly 20 for additional rotational motion of assemblies 100 and 200 about axis 102, which is the longitudinal axis of the instrument. Other than joint 150 and the rotational mounting of shaft assembly 100 in actuator assembly 20, shaft assembly 100 is substantially rigid transverse to its longitudinal axis. Shaft assembly 100 is also substantially rigid parallel to axis 102.

Actuator assembly 20 includes proximal handle 30, manually operable clamp actuator lever 40, and manually operable fastener actuator lever 60. Pivoting clamp actuator lever 40 down into actuator assembly 20 pulls the lower portion of anvil part 280 toward fastener holding part 210. Squeezing fastener actuator lever 60 toward handle 30 causes fastener holding part 210 to drive the surgical fasteners contained in that part in the distal direction toward anvil part 280. Fastener actuator lever 60 cannot be operated until safety latch 90 is pivoted down away from lever 60 as shown in phantom lines in FIG. 3.

Figure 4:
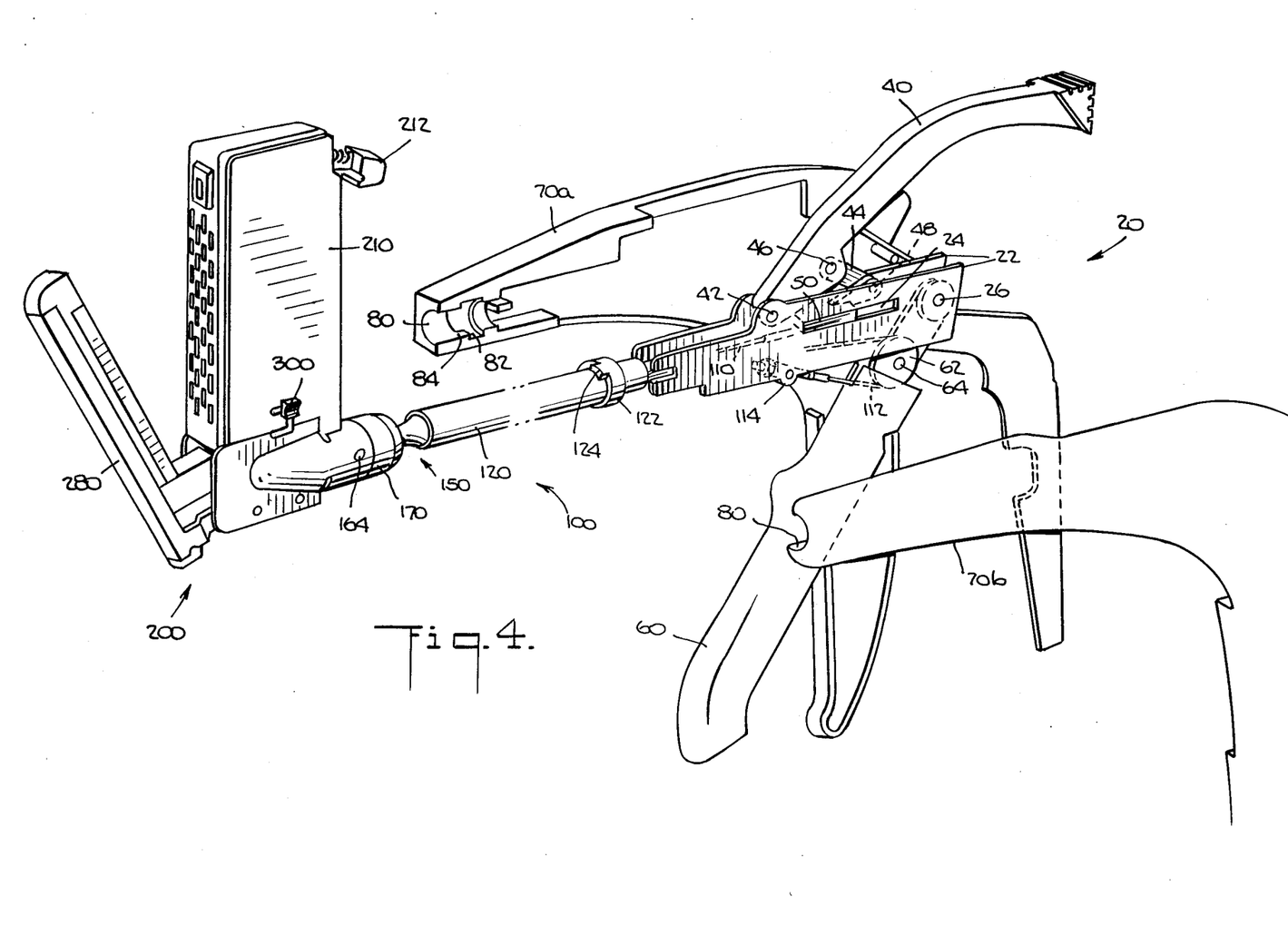
FIG. 4 is a partial exploded perspective view of the apparatus of FIGS. 1-3.
Figure 7:
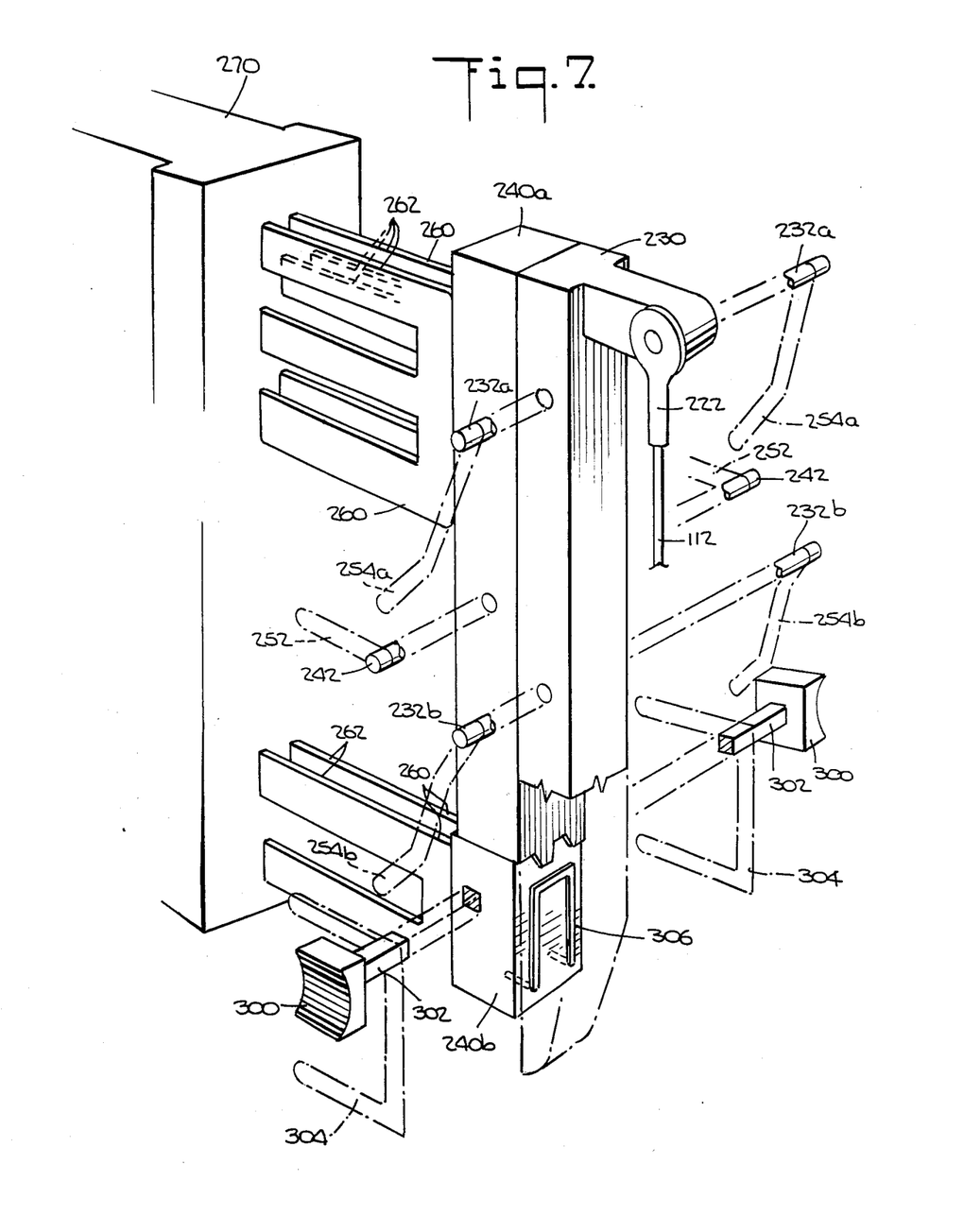
Figure 8:
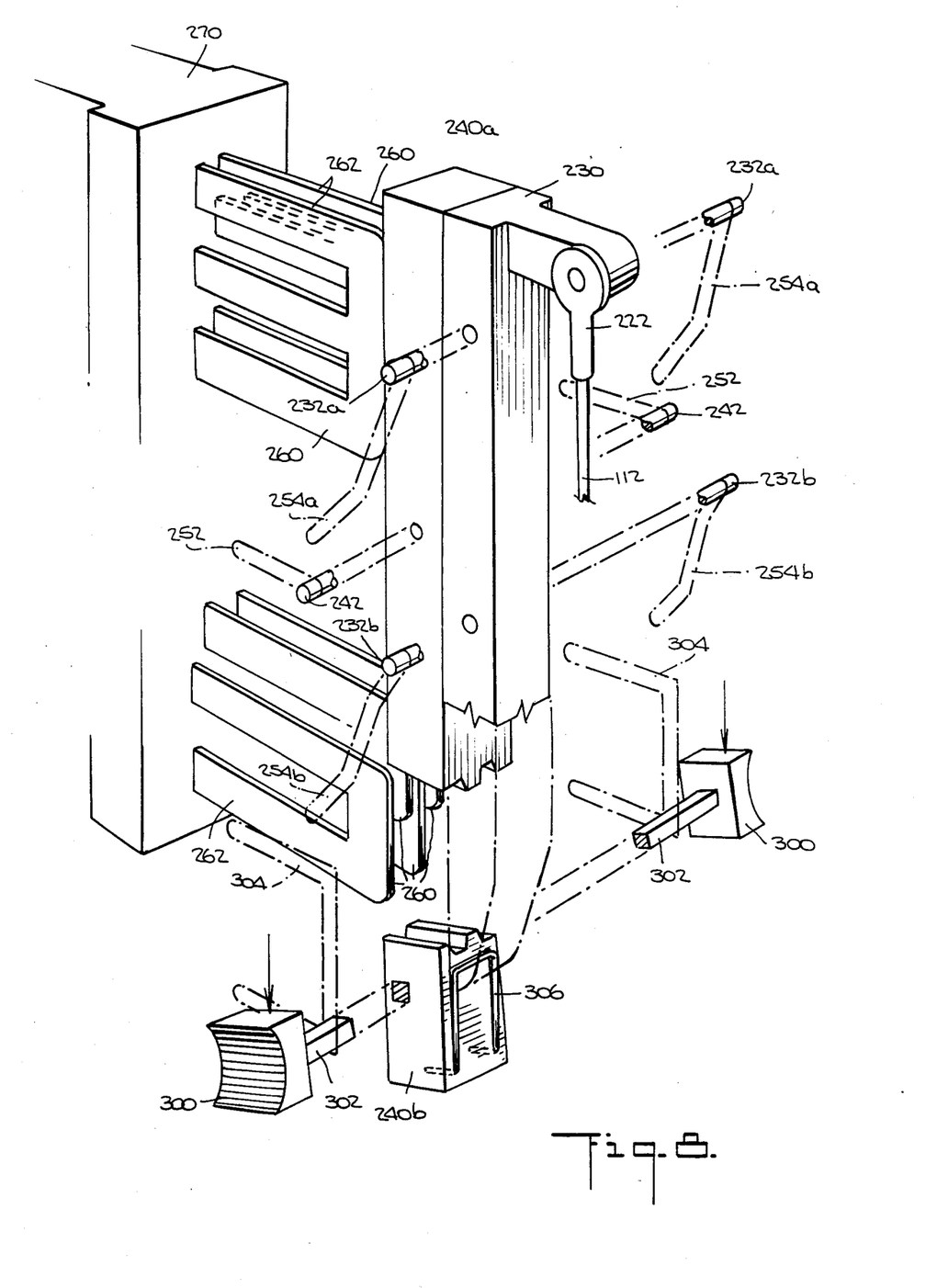
Figure 9:
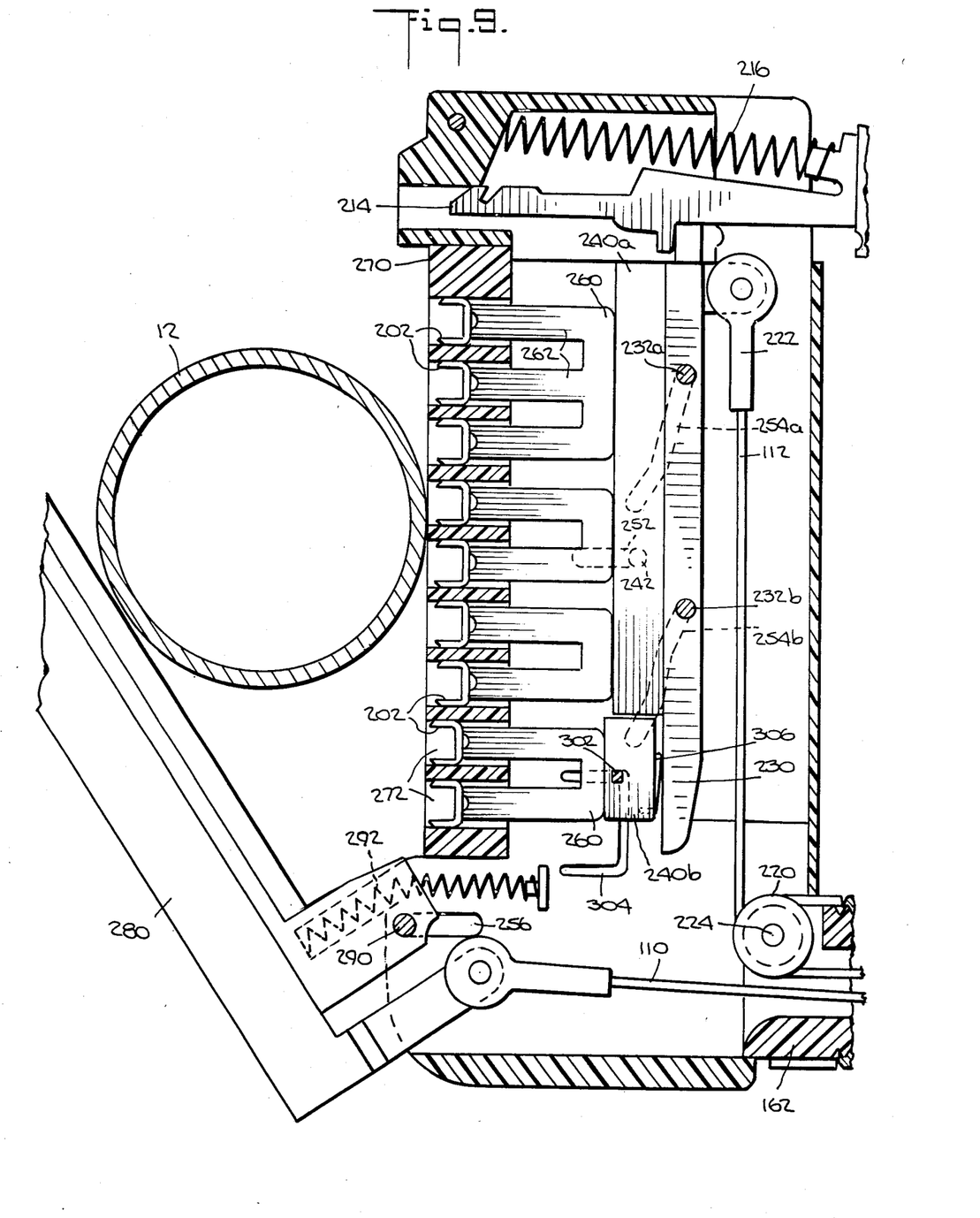
FIG. 9 is a partly sectional, elevational view of a portion of the apparatus of FIGS. 1-8 showing an initial stage in the operating cycle of that apparatus.

In the illustrative embodiment, fastener applying assembly 200 applies four parallel rows of metal surgical staples 202 (see FIGS. 4 and 9). The length of the staple array parallel to the (vertical) longitudinal axis of fastener holding part 210 can be altered by moving selector buttons 300 from the upper position shown in FIGS. 1 and 7 to the lower position shown in FIG. 8 or vice versa. In the upper position of selector buttons 300 the entire array of staples is applied to the tissue. In the lower position of selector buttons 300 the lower portion of the staple array is disabled and only the upper portion of the array is applied to the tissue. In the particular embodiment shown in the drawings, when selector buttons 300 are moved to their lower position, the two lower-most staples in each of the four rows of staples are not applied to the tissue. It will be understood that the number and arrangement of the staples thus disabled in accordance with this invention can be varied as desired.

Figures 2, 6:
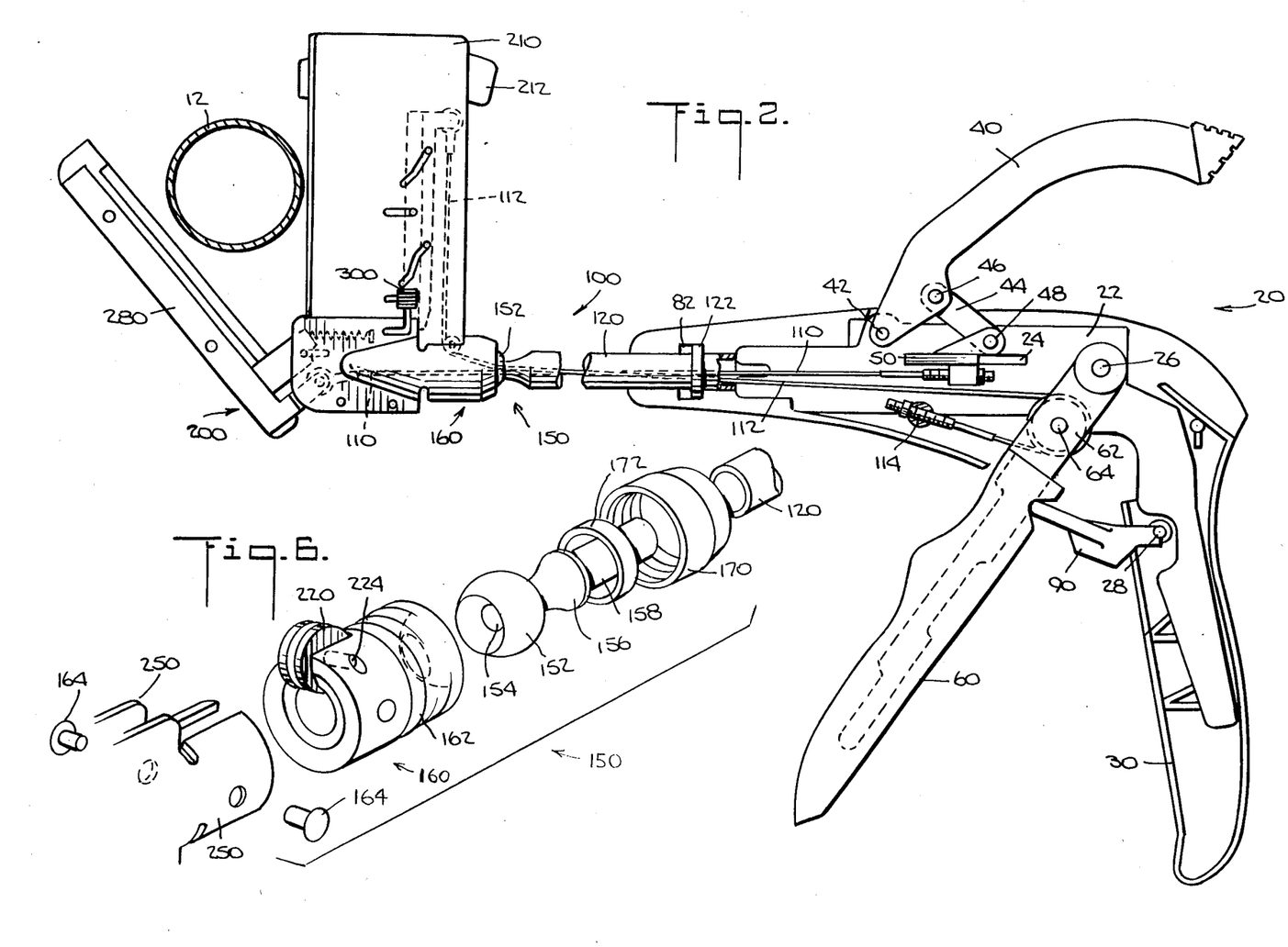
FIG. 2 is a partial, partly sectional, elevational view of the apparatus of FIG. 1 showing an initial stage in the operating cycle of that apparatus.
FIGS. 5-8 are exploded perspective views of various portions of the apparatus of FIGS. 1-4.

Before considering the construction of the apparatus in more detail, a brief description of its overall operation will be given. Assuming that all of the staples in staple holding part 210 are to be applied, the initial condition of the apparatus is shown in FIGS. 1, 2, and 9. Fastener applying assembly 200 is rotated, if desired, by any desired amount about any of axes 102, 104, and 106 so that fastener applying assembly 200 has any desired angular orientation relative to actuator assembly 20. Joint 150 and the rotational connection between shaft assembly 100 and actuator assembly 20 are preferably tight enough so that during subsequent operation of the apparatus, assemblies 20 and 200 maintain whatever relative angular orientation they are placed in.

Figure 10:
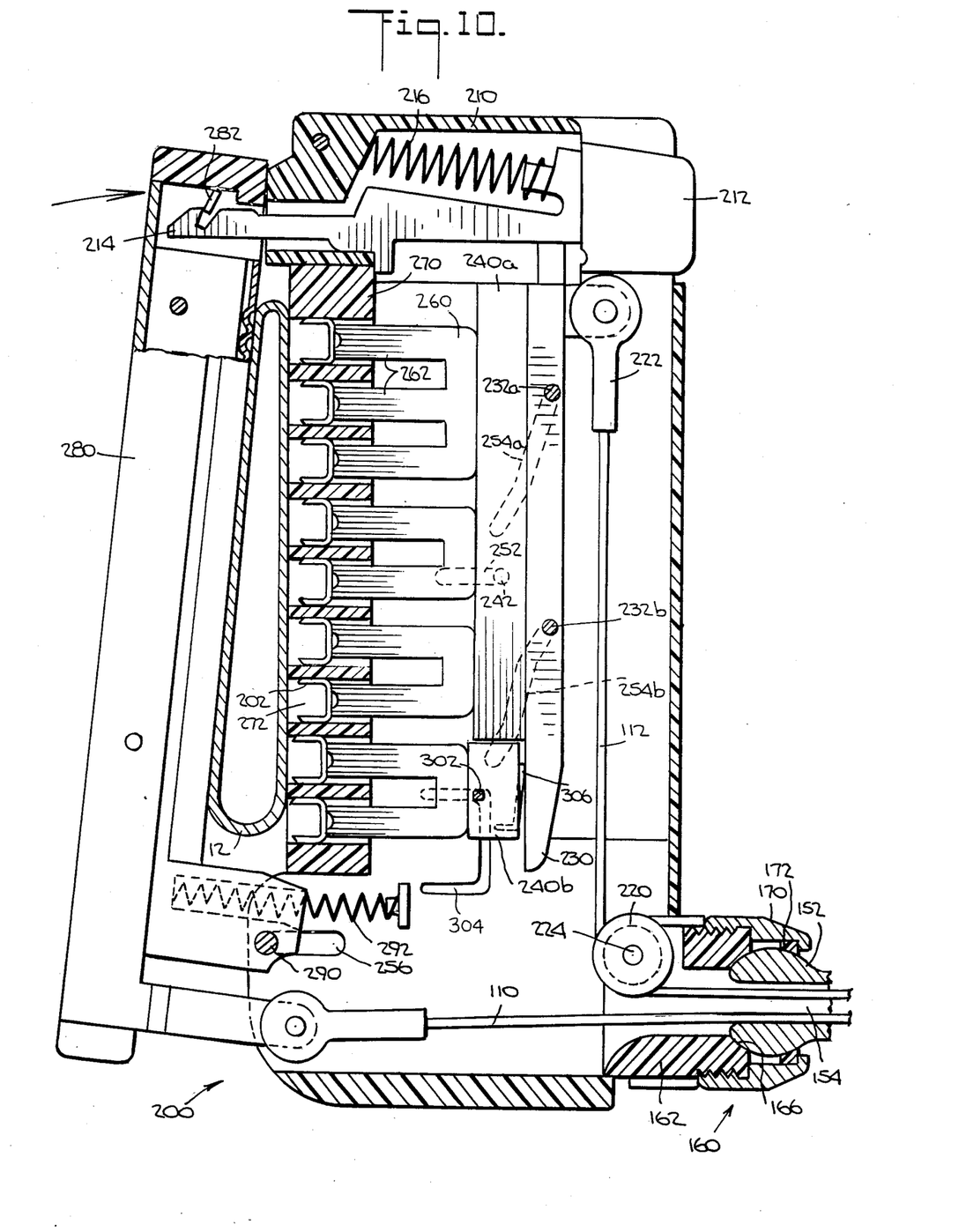
FIGS. 10-13 are views similar to FIG. 9 showing successive stages in the operating cycle of the apparatus.

The tissue 12 to be fastened is placed between anvil part 280 and fastener holding part 210. The upper portion of anvil part 280 is manually moved toward the opposite upper portion of fastener holding part 210 as shown in FIG. 10, and latch button 212 is manually pushed in the distal direction so that latch 214 engages catch 282 in anvil part 280. This hold the upper end of anvil part 280 against the upper end of fastener holding part 210 to begin the clamping of the tissue between those parts.

Figure 3:
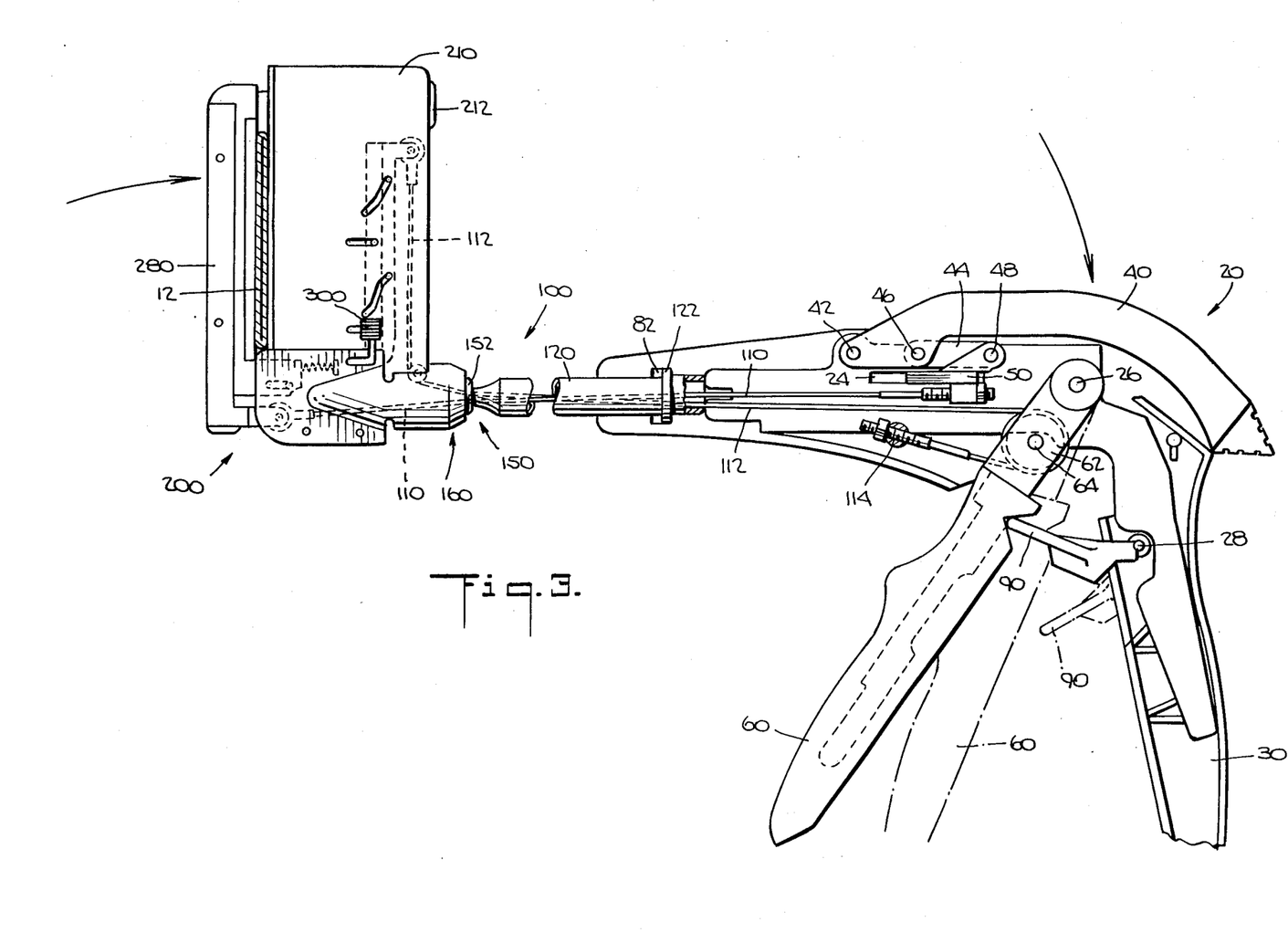
FIG. 3 is a view similar to FIG. 2 but showing a subsequent stage in the operating cycle.
Figure 11:
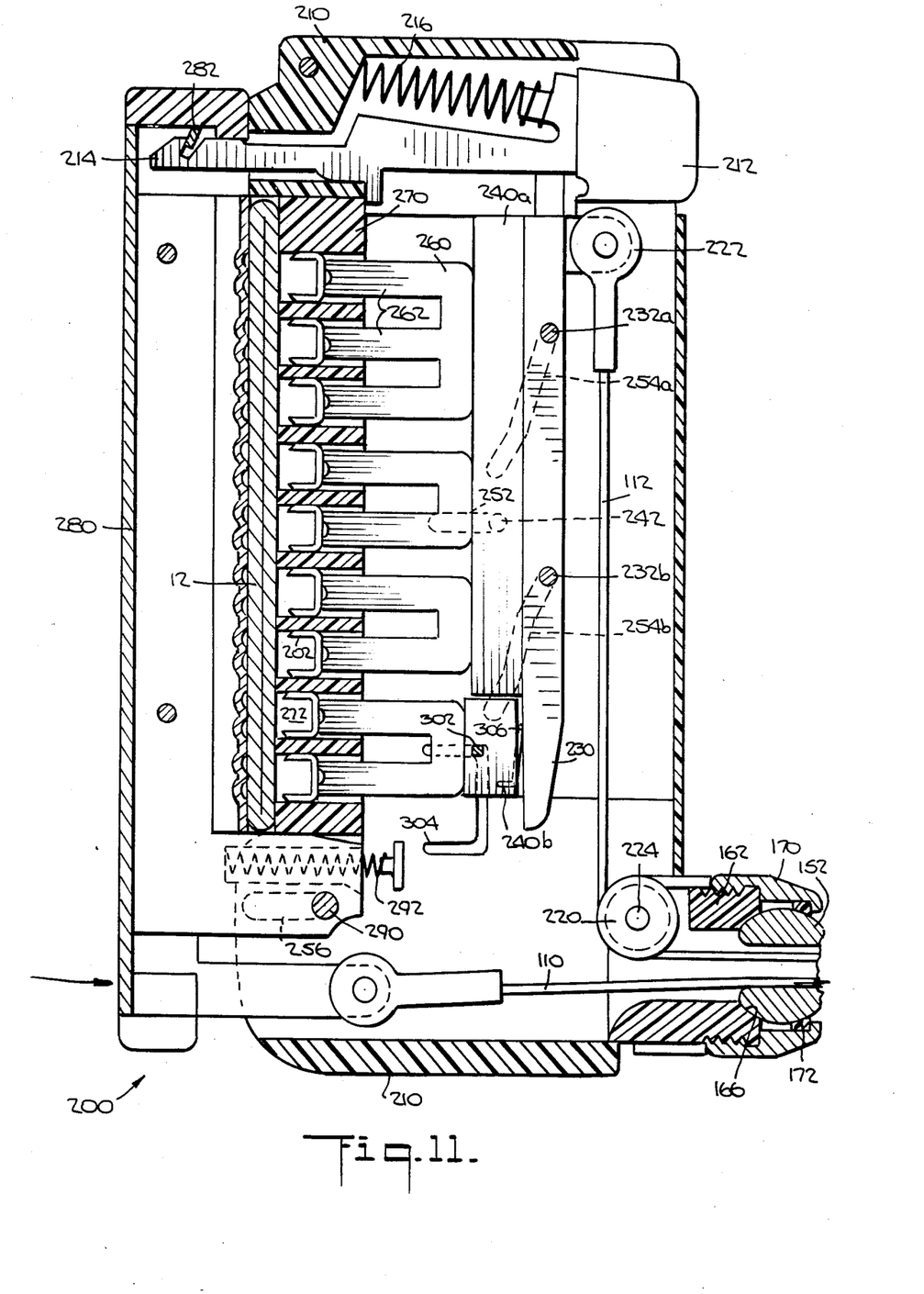

The next operating step is to pivot clamp actuator lever 40 down into actuator assembly 20 as shown in FIG. 3. This pulls the lower end of anvil part 280 in against the lower end of fastener holding assembly 210 as shown in FIGS. 3 and 11. Parts 210 and 280 are now substantially parallel to one another with tissue 12 firmly clamped between the opposing surfaces of those parts. The tissue is now ready to be fastened.

Figure 12:
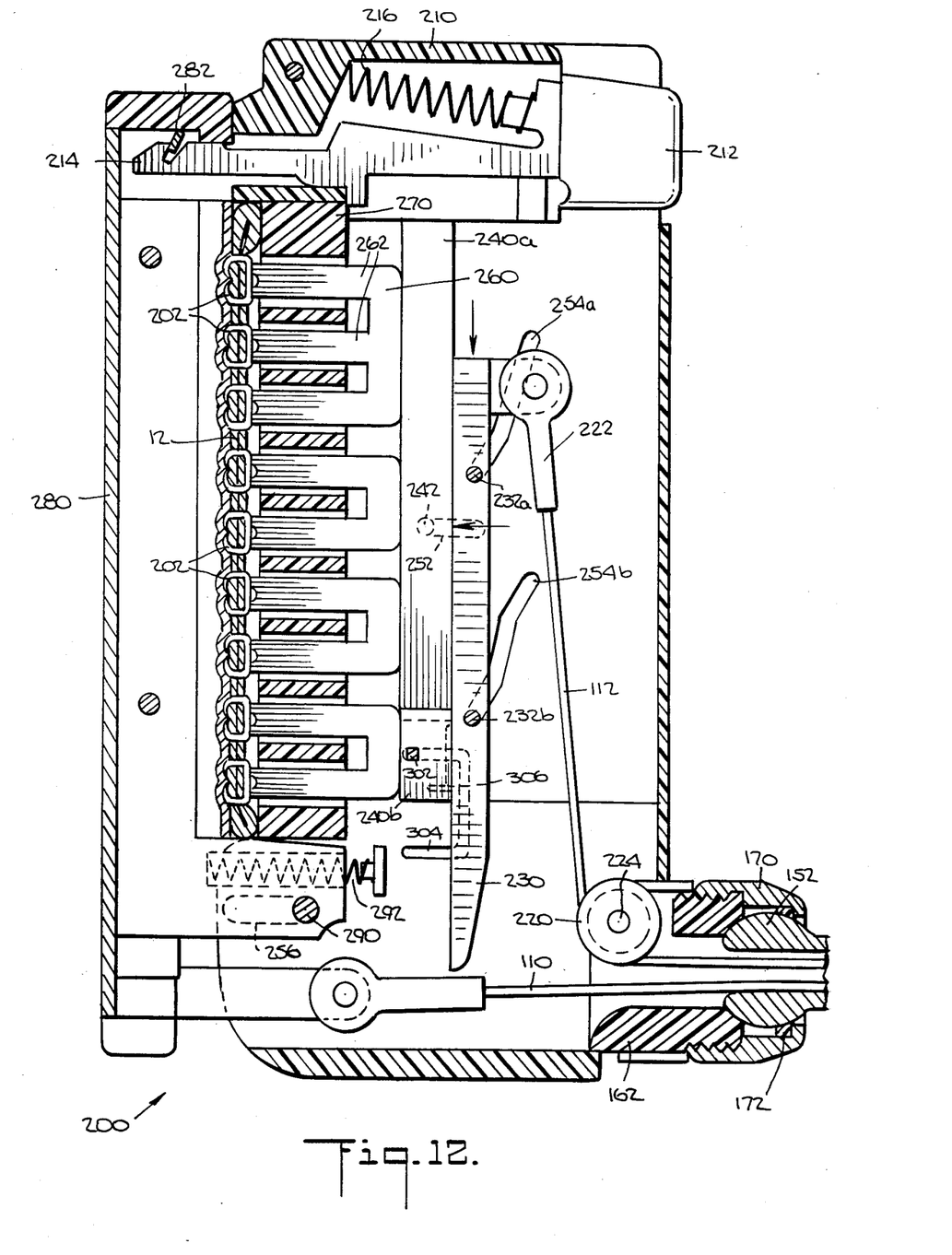

When the fasteners are to be applied, safety latch 90 is pivoted down as indicated in phantom lines in FIG. 3. Fastener actuator lever 60 is then pivoted toward handle 30 as also shown in phantom lines in FIG. 3. This causes fastener holding assembly 210 to drive the legs of a plurality of metal surgical staples 202 through tissue 12 and against anvil part 280 as shown in FIG. 12. Anvil part 280 clinches or crimps the ends of the staple legs to secure the staples in the tissue. (Although metal staples are employed in the depicted embodiment, it will be understood that two-part plastic fasteners, such as those shown in Green U.S. Pat. No. 4,402,445, can alternatively be used.) The tissue fastening procedure is now complete.

Figure 13:
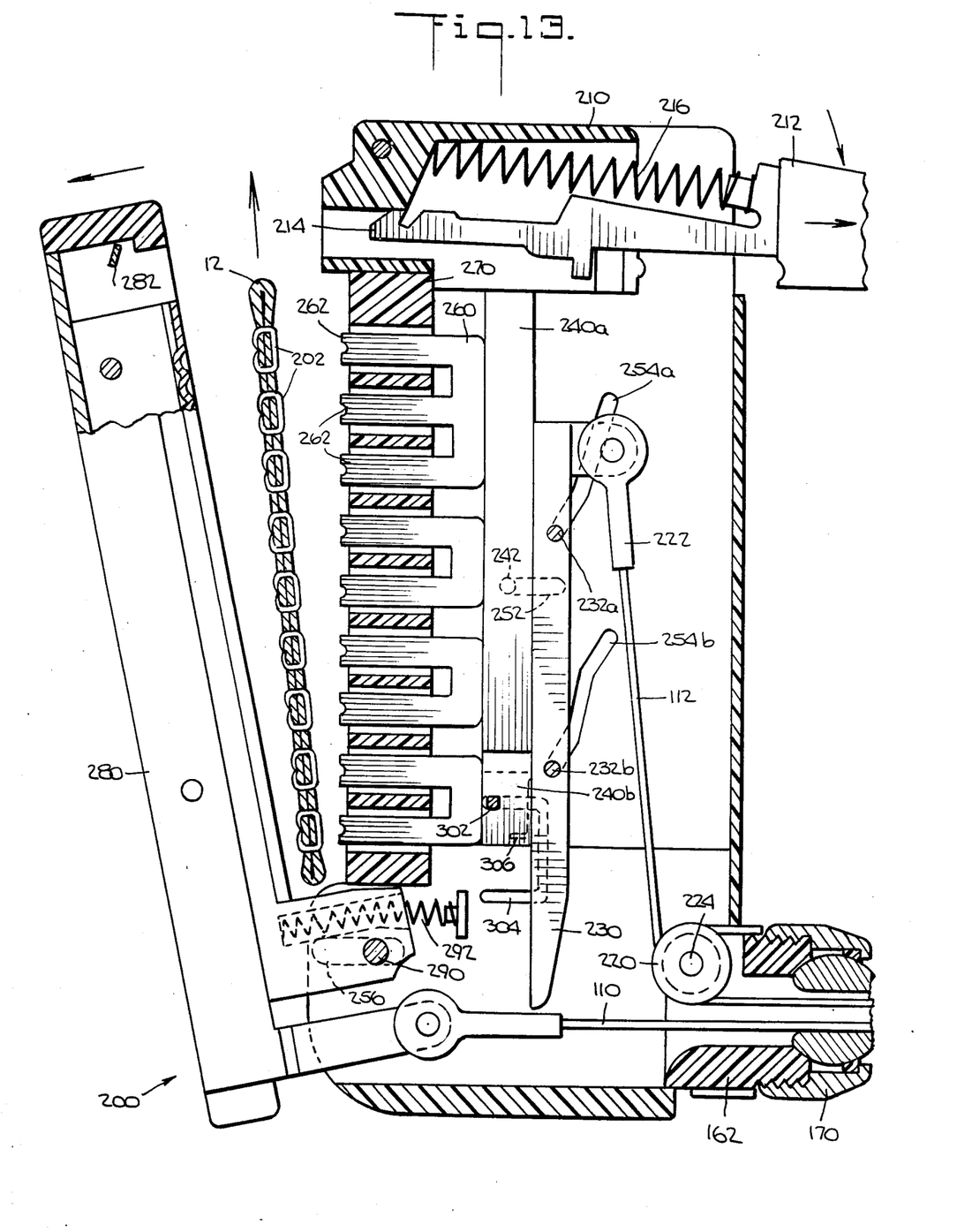

The fastened tissue is removed from the apparatus by manually pushing up on latch button 212 as shown in FIG. 13. This causes latch 214 to release catch 282, thereby allowing anvil part 280 to pivot away from fastener holding part 210. The fastened tissue can now be removed from the apparatus.

Figure 14:
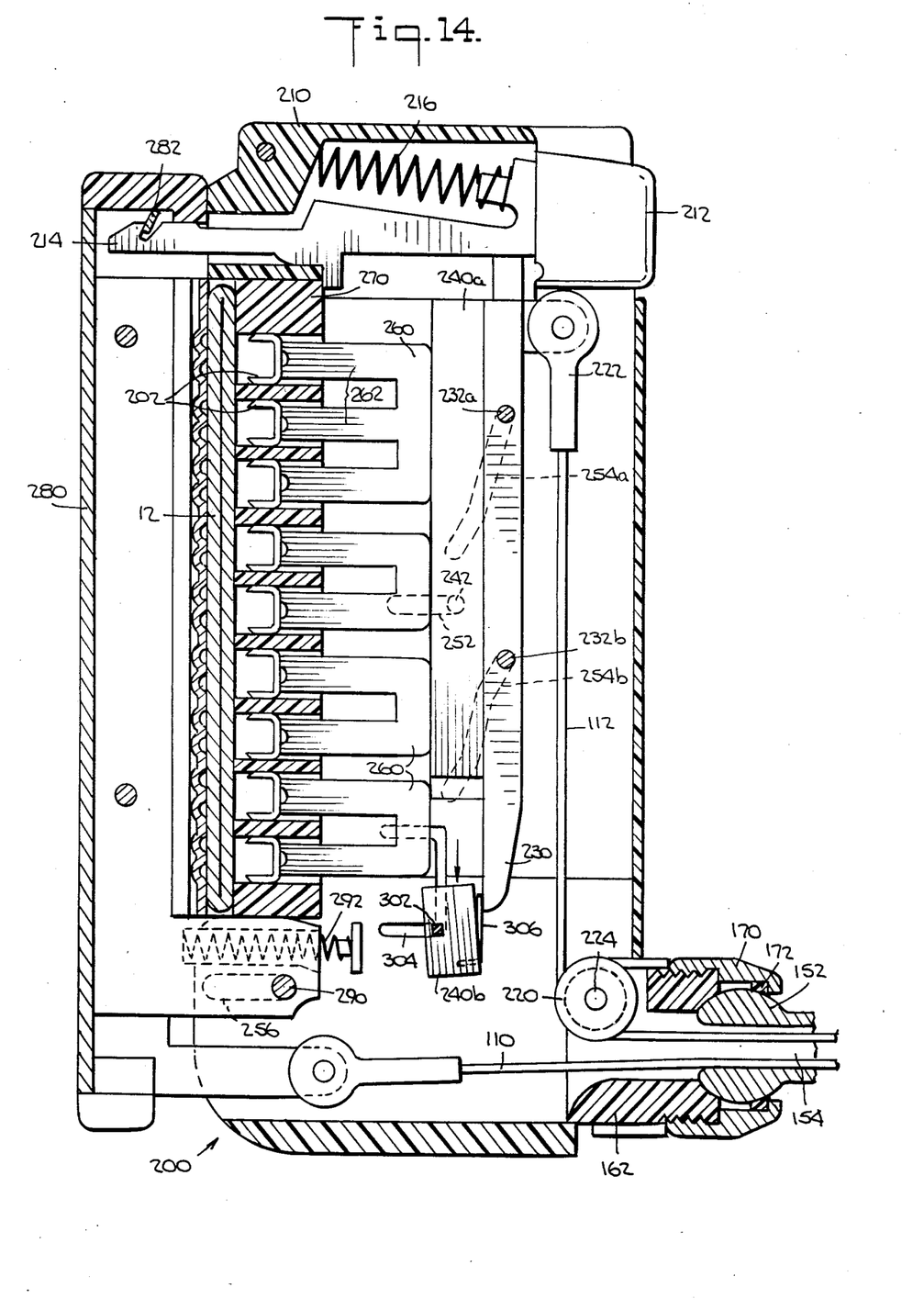
FIG. 14 is a view similar to FIG. 11 showing operation of the apparatus to alter the array of surgical fasteners to be applied by that apparatus.
Figure 15:
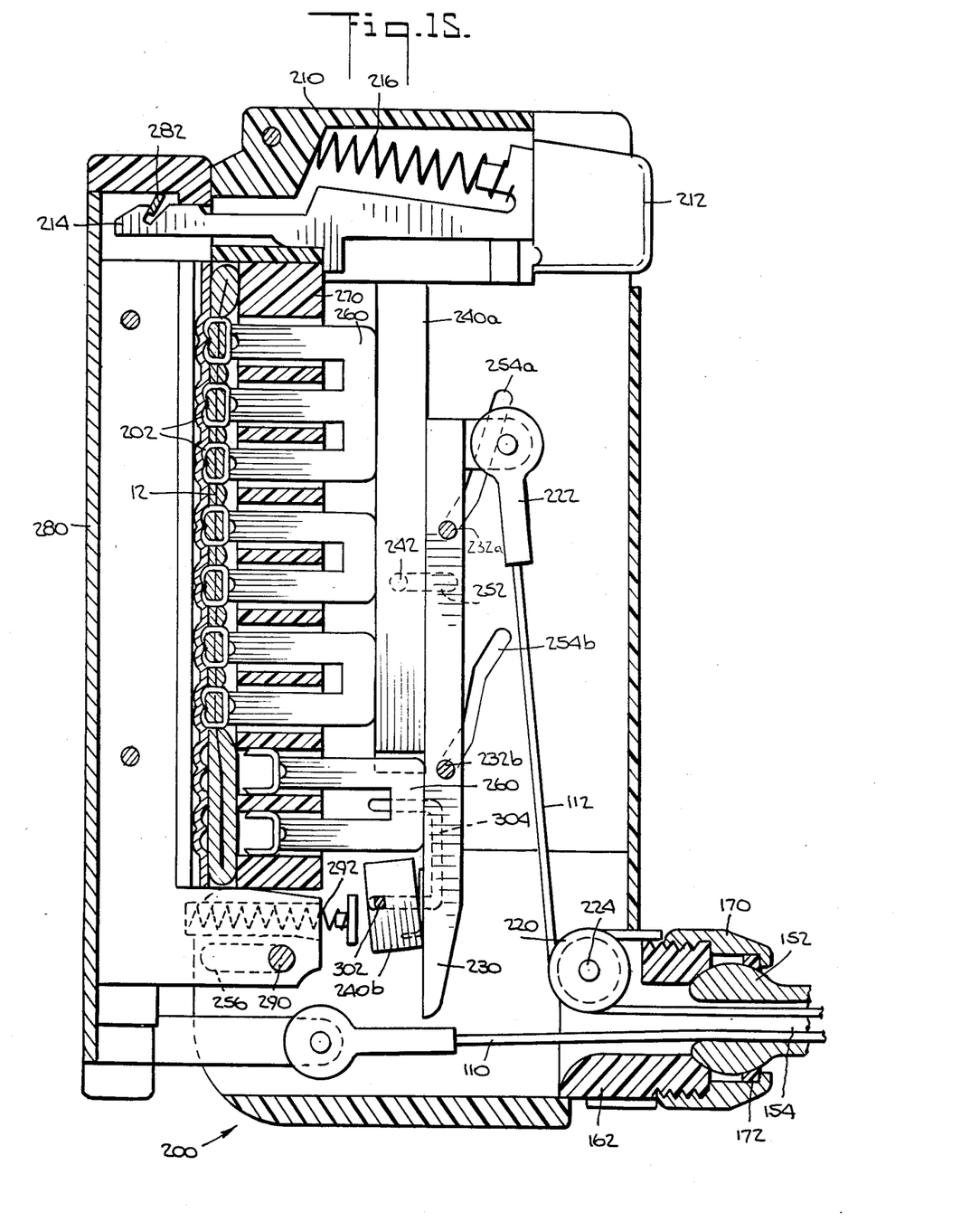
FIG. 15 is a view similar to FIG. 12 showing operation of the apparatus subsequent to the step shown in FIG. 14.

If in the foregoing procedure the lower portion of the staple array were not to be applied to the tissue, selector buttons 300 would be moved to their lower position as shown in FIG. 8 at any convenient time prior to operation of fastener actuator lever 60. As shown in FIGS. 14 and 15, this prevents the lower two staples in each row of staples from being driven into the adjacent tissue. In all other respects, the operation of the apparatus is as described above.

Considering now the internal construction and operation of the apparatus, first with reference to FIG. 2, clamp actuator lever 40 is pivotally connected to actuator assembly frame 22 by pivot pin 42. One end of toggle link 44 is pivotally connected to lever 40 by pin 46. The other end of toggle link 44 is pivotally connected to slide 50 by pin 48. Slide 50 is mounted for longitudinal reciprocal motion in slots 24 in frame 22 (see also FIG. 4). When lever 40 is pivoted out from the remainder of actuator assembly 20 as shown in FIGS. 2 and 4, slide 50 is in its distal position in slots 24. When lever 40 is pivoted down toward the remainder of actuator assembly 20 as shown in FIG. 3, slide 50 moves proximally in slots 24. In the fully operated position of lever 40, pin 46 has moved slightly past a straight line through pins 42 and 48 so that lever 40 tends to remain in the fully operated position.

The proximal end of a first transversely flexible member 110 is connected to slide 50. Member 110 may be a metal wire or cable, and for convenience herein, member 110 will be referred to as cable 110. Cable 110 passes through the hollow tubular shaft 120 which is the outer member of most of the length of shaft assembly 100. Cable 110 also passes through longitudinal aperture 154 (FIG. 6) in ball 152 and into fastener applying assembly 200. The distal end of cable 110 is connected to anvil part 280 (see also FIG. 5). Accordingly, when lever 40 is pivoted down toward the remainder of actuator assembly 20, cable 110 pulls the lower end of anvil part 280 in toward fastener holding part 210. Cable 110 is transversely flexible so that it does not interfere with the pivoting of joint 150. It should also be noted that cable 110 passes through the point of intersection of axes 102, 104, and 106 (FIG. 1) so that even when placed in tension by operation of lever 40, cable 110 does not tend to alter the relative rotational orientation of assemblies 20 and 200.

Figure 5:
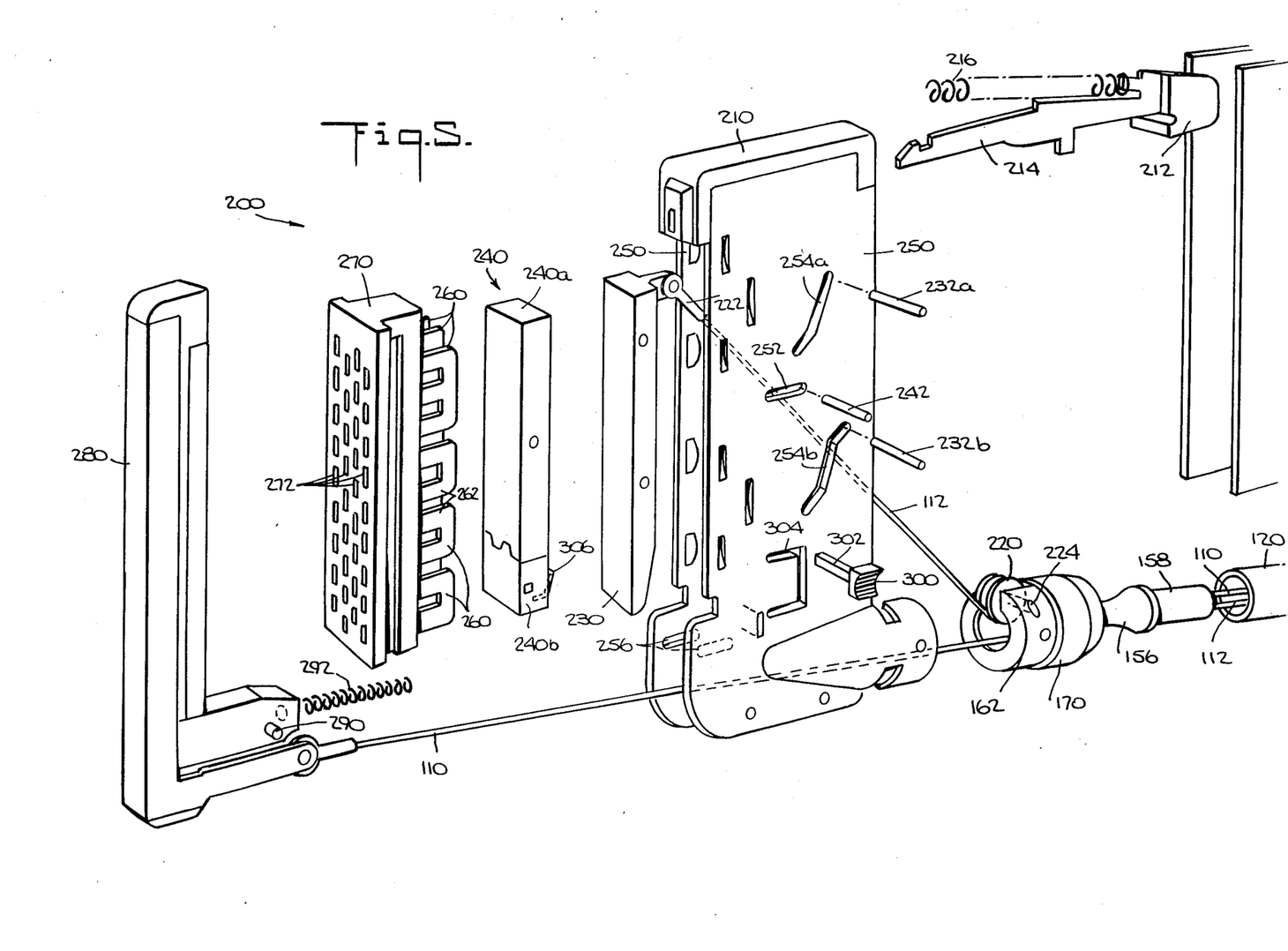

Returning to FIG. 2, fastener actuator lever 60 is pivotally connected to frame 22 by pin 26. Safety latch 90 is similarly pivotally connected to handle 30 by pin 28. The proximal end of a second transversely flexible member 112 is fixedly attached to frame 22 at anchor 114. Member 112 may be similar to cable 110 and is therefore referred to as cable 112. A proximal portion of cable 112 passes around roller 62 which is rotatably mounted on lever 60 by means of axle 64. After passing roller 62, cable 112 passes distally through shaft 120 and joint 150 and into fastener holding part 210. As is best seen in FIGS. 5 and 9, as cable 112 enters fastener holding part 210, it passes around roller 220. Roller 220 redirects cable 112 up to anchor 222 which connects the distal end of cable 112 to cam bar 230. Accordingly, when lever 60 is pivoted toward handle 30, cable 112 pulls down on cam bar 230. Like cable 110, cable 112 passes through the point of intersection of axes 102, 104, and 106 and is sufficiently transversely flexible so that it does not interfere with the pivoting of joint 150 or tend to alter the relative rotational orientation of assemblies 20 and 200 even when placed in tension by operation of lever 60.

Cam bar 230 is disposed between two parallel, laterally spaced frame members 250 (FIG. 5) of fastener holding part 210. The distal surface of cam bar 230 bears on and is slidable along the proximal surface of pusher actuator member 240, which is also disposed between frame members 250. Pusher actuator member 240 consists of two interfitting parts 240a and 240b. Upper part 240a is associated with the upper portion of the staple array in fastener holding part 210. This is the portion of the staple array which is always applied by the apparatus. Lower part 240b, on the other hand, is associated with the lower portion of the staple array in fastener holding part 210. Lower part 240b is shiftable from the upper, operative position shown in FIGS. 5 and 7 to the lower, inoperative position shown in FIGS. 8 and 14 by operation of selector buttons 300. Selector buttons 300 are mounted on the ends of pin 302 which extends through lower part 240b and U-shaped guide slots 304 in frame members 250. Lower part 240b is resiliently urged in the distal direction by compression spring 306 which is attached to lower part 240b and which bears on the distal face of cam bar 230. Spring 306 has the effect of urging pin 302 a short distance into either the upper leg of U-shaped guide slots 304 or the lower leg of those slots depending on whether lower part 240b is in its upper or lower position. This provides a detent function for releasably holding lower part 240b in either position and for preventing lower part 240b from inadvertently shifting from one position to the other.

The distal surface of pusher actuator member part 240a bears on the proximal ends of all of pusher members 260 except the bottommost pusher member 260 associated with each row of staples. In the operative position of lower pusher actuator member part 240b, the distal surface of that part bears on the proximal ends of the bottommost pusher member 260 in each row. In its inoperative position, however, lower pusher actuator member part 240b is below and therefore does not contact the bottommost pusher member 260 in each row. Pusher members 260 have pusher fingers 262 extending into apertures 272 in fastener holder 270 behind staples 202. The saw tooth shape of the interconnection between parts 240a and 240b is provided because the rows of staples are longitudinally offset relative to one another.

Except for the above-described vertical shifting of lower pusher actuator member part 240b, pusher actuator member 240 is constrained to move substantially parallel to the axis along which staples 202 are driven by pusher members 260. This constraint is provided by guide pins 242 which extend laterally outward from part 240a into guide slots 252 in frame members 250, and by pin 302 in either the upper or lower horizontal legs of U-shaped guide slots 304. It should be noted that pusher actuator member parts 240a and 240b can also pivot to a limited degree about pins 242 and 302, respectively.

As cam bar 230 is pulled down by cable 112, it is also forced to move in the distal direction by operation of cam follower pins 232a and 232b which pass through cam bar 230 and respectively project laterally into cam slots 254a and 254b in frame members 250. Cam slots 254 are inclined so that as cam bar 230 moves down in response to the motion of cable 112, it also moves distally. Cam bar 230 slides longitudinally along pusher actuator member 240 so that only the distal motion of cam bar 230 is imparted to member 240. As member 240 moves distally, it drives the pusher members 260 that are in contact with parts 240a and 240b (and the staples 202 associated with those pusher members) in the distal direction. This means that when lower pusher actuator member part 240b is in its operative, upper position, all of the staples in fastener holder part 210 are driven as shown in FIG. 12; but when part 240b is in its inoperative, lower position, only the staples associated with upper part 240a are driven as shown in FIG. 15. In the latter case, the staples associated with part 240b remain undisturbed in fastener holder 270. This causes a portion of the tissue to remain unstapled as shown in FIG. 15.

Cam slots 254a may be shaped differently from can slots 254b to cause one end (e.g., the lower end) of cam bar 230 to initially move more rapidly in the distal direction than the upper end. As described in more detail in concurrently filed, commonly assigned U.S. patent application Ser. No. 662,679, this causes the staples to be applied progressively rather than exactly simultaneously, thereby reducing the peak force required to operate the apparatus.

The connection between shaft assembly 100 and actuator assembly 20 which permits relative rotation of those assemblies is best seen in FIG. 4. The proximal end of shaft 120 is rotatably mounted in a cylindrical socket 80 formed in the two mirror image halves 70a and 70b of the outer shell of actuator assembly 20. Shell halves 70 are held together by any suitable means such as rivets, adhesive, or the like. Annular collar 122 on shaft 120 is received in annular enlargement 82 of socket 80 to retain shaft 120 in the proper longitudinal position relative to actuator assembly 20. If desired, the amount of rotation of shaft 120 relative to actuator assembly 20 can be limited by cooperation of stop 124 on shaft 120 and stop 84 on actuator assembly shell 70. Shell halves 70 preferably engage shaft 120 with sufficient force to frictionally maintain the relative angular orientation of shaft 120 and actuator assembly 20 established by the user of the apparatus.

The detailed construction of joint 150 is shown in FIG. 6. Ball 152 is formed at the distal end of hollow, generally frustoconical pedestal 156. A hollow cylindrical shank 158 extends proximally from the base of pedestal 156. Shank 158 is forcefitted into the distal end of shaft 120. Ball 152 fits snugly into socket 160, the construction of which is best seen in FIG. 10. Socket 160 includes distal seat member 162 which carries roller 220 on axle 224 and which is fixedly attached to frame members 250 by pins 164 (FIG. 6). Seat member 162 is hollow and has a proximal-facing annular seat surface 166 for receiving the distal end portion of ball 152. The proximal portion of the cylindrical outer surface of seat member 162 is threaded to receive collar 170. Collar 170 forces an annular retaining ring 172 against a proximal portion of the surface of ball 152. Accordingly, ball 152 is captured between seat surface 166 and retaining ring 172 but can rotate relative to those members about each of axes 102, 104, and 106. Surfaces 166 and 172 preferably engage ball 152 with sufficient force to frictionally maintain whatever relative angular orientation of assemblies 20 and 200 is established by the user of the apparatus. In a particularly preferred embodiment, ball 152 is steel and members 162 and 172 are made of a thermoplastic material such as nylon.

Anvil part 280 is pivotally connected to fastener holding part 210 by means of pin 290 in elongated slots 256 in frame members 250. Slots 256 are elongated parallel to the longitudinal axis of the apparatus so that anvil part 280 can both pivot about pin 290 and translate parallel to slots 256. Anvil part 280 is resiliently biased away from fastener holding part 210 by compression coil spring 292 which is compressed between those parts. Latch 214 is resiliently biased in the proximal direction as shown, for example, in FIG. 9 by compression coil spring 216 acting between latch 214 and the body of fastener holding part 210.

It will be readily apparent to those skilled in the art that the invention is not limited to the particular embodiment described above. For example, the invention is equally applicable to surgical fastener applying apparatus of the types shown in any of O'Dea U.S. Pat. No. 3,315,863, Green U.S. Pat. No. 4,354,628, Green U.S. Pat. No. 4,402,444, and Green U.S. Pat. No. 4,402,445, to name but few of the suitable known devices.

We claim:

1. Apparatus for applying an array of surgical fasteners to body tissue comprising:
   a plurality of surgical fasteners in a predetermined array, said array being subdivided into first and second subarrays;
   first and second pusher means for respectively pushing the fasteners in the first and second subarrays into the tissue;
   first means for supplying the work required for pushing the fasteners into the tissue; and
   second means for optionally transmitting the work supplied by the first means to either the first and second pusher means together or to the first pusher means only.

2. The apparatus defined in claim 1 wherein the fastener array is planar, wherein the fasteners are pushed into the tissue along an axis substantially perpendicular to the plane of the array, and wherein the first means comprises a substantially rigid first member substantially parallel to and at least coextensive with the array.

3. The apparatus defined in claim 2 wherein the second means comprises:
   a second member interposed between the first member and the first pusher means; and
   a third member selectively interposable between the first member and the second pusher means.

4. The apparatus defined in claim 3 wherein the second means further comprises:
   third means for mounting the third member for motion substantially parallel to the array between a first position in which the third member is interposed between the first member and the second pusher means and a second position in which the third member is not interposed between the first member and the second pusher means.

5. The apparatus defined in claim 4 wherein the first means further comprises detent means for releasably retaining the third member in either the first or the second position.

* * * * *